United States Patent [19]

Koster et al.

[11] Patent Number: 4,670,554

[45] Date of Patent: Jun. 2, 1987

[54] ((3-ACYLAMINO-2-OXO-1-AZETIDINYL)OX-Y)METHYL)PHOSPHINIC ACIDS

[75] Inventors: William H. Koster, Ringoes, N.J.; Hermann Breuer, Schoenhofen, Fed. Rep. of Germany

[73] Assignee: E. R. Squibb & Sons, Inc., Princeton, N.J.

[21] Appl. No.: 499,643

[22] Filed: May 31, 1983

[51] Int. Cl.$^4$ .................... C07F 9/65; A61K 31/675; C07D 205/08
[52] U.S. Cl. .................................................. 540/355
[58] Field of Search ....................... 260/245 A, 239 A; 540/355

[56] References Cited

U.S. PATENT DOCUMENTS 4,337,197  6/1982  Gordon et al. ................. 260/239 A

FOREIGN PATENT DOCUMENTS 0061765 10/1982 European Pat. Off. .
2071650  9/1981 United Kingdom .

*Primary Examiner*—Mark L. Berch
*Attorney, Agent, or Firm*—Lawrence S. Levinson; Donald J. Barrack

[57] ABSTRACT

Antibacterial activity is exhibited by β-lactams having a 3-acylamino substituent and in the 1-position a substituent having the formula

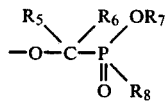

wherein
$R_5$ and $R_6$ are the same or different and each is hydrogen, alkyl, alkenyl, alkynyl, phenyl, substituted phenyl, cycloalkyl or a 4,5,6 or 7-membered heterocycle, or $R_5$ and $R_6$ together with the carbon atom to which they are attached are cycloalkyl or a 4,5,6 or 7-membered heterocycle, or one of $R_5$ and $R_6$ is hydrogen and the other is azido, halomethyl, dihalomethyl, trihalomethyl, alkoxycarbonyl, alkenyl, alkynyl, 2-phenylethenyl, 2-phenylethynyl, carboxyl, $-CH_2X_1$, $-S-X_2$, $-O-X_2$, or

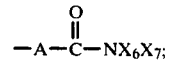

$R_7$ is hydrogen, alkyl, substituted alkyl, phenyl, substituted phenyl, 1-(ethoxycarbonyloxy)ethyl, 1,3-dihydro-3-oxo-1-isobenzofuranyl,

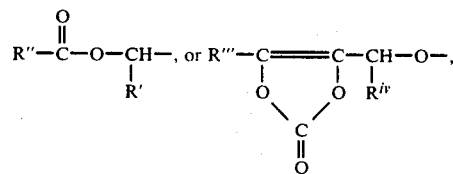

wherein R' is hydrogen or alkyl, R'' is alkyl or phenyl, R''' is hydrogen, methyl or phenyl, and R$^{iv}$ is hydrogen or together with R''' is $-(CH_2)_3-$ or $-(CH_2)_5-$; and $R_8$ is hydroxy, alkoxy, (substituted alkyl)oxy, phenyloxy, (substituted phenyl)oxy, alkyl, substituted alkyl, phenyl, substituted phenyl, heteroaryl, amino, substituted amino, alkylthio, (substituted alkyl)thio, phenylthio, (substituted phenyl)thio, or

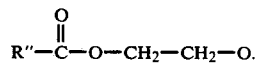

14 Claims, No Drawings

((3-ACYLAMINO-2-OXO-1-AZETIDINYL)OXY)METHYL)PHOSPHINIC ACIDS

RELATED APPLICATIONS

U.S. patent application Ser. No. 404,945, filed Aug. 4, 1982. now abandoned discloses that β-lactams having a

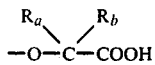

substitutent (or an ester or pharmaceutically acceptable salt thereof) in the 1-position and an acylamino substituent in the 3-position exhibit activity against a range of gram-negative and gram-positive bacteria.

U.S. patent application Ser. No. 358,140, filed Mar. 15, 1982, U.S. Pat. No. 4,478,749 discloses that β-lactams having a phosphinic or phosphonic substituent in the 1-position and an acylamino substituent in the 3-position exhibit activity against a range of gram-negative and gram-positive bacteria.

BACKGROUND OF THE INVENTION

The β-lactam ring,

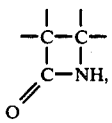

has been known since the late nineteenth century. While knowledge of β-lactam chemistry developed during the early 1900's, it was not until 1929 that Fleming reported in Brit. J. Exper. Pathol., 10, 226 (1929) that a fermentation product of the organism Penicillium notatum had antibiotic properties The compound which Fleming had worked with was benzylpenicillin.

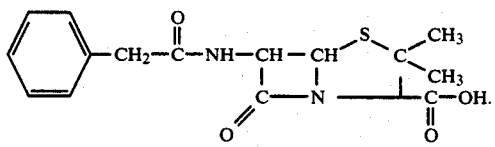

The in vivo activity of benzylpenicillin against various bacteria was reported by Chain et al. in Lancet, 2:226 (1940).

During the early 1940's research in the field of penicillins was intense. This research focused first on structure elucidation and then on synthetic routes for preparing benzyl penicillin. It was not, however, until the late 1950's that a totally synthetic route was discovered for the preparation of benzyl penicillin.

U.S. Pat. No. 2,941,955, issued June 21, 1960, to Doyle et al., discloses the discovery of 6-aminopenicillanic acid.

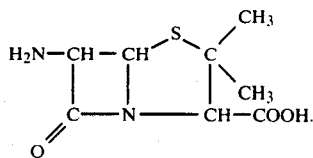

This patent was followed by U.S. Pat. No. 2,951,839, issued Sept. 6, 1960, also to Doyle et al., which discloses the use of 6-aminopenicillanic acid as a valuable intermediate which could be acylated, using art-recognized procedures, to obtain penicillin derivatives having antibiotic properties. Using 6-aminopenicillanic as a stepping stone, research chemists have prepared numerous penicillin derivatives having antibiotic activity.

The second major class of β-lactam antibiotics is the cephalosporins. In the 1940's a Cephalosporium species was found to produce an antibiotic that had activity against gram-positive and gram-negative bacteria. Work in the 1950's showed that the fermentation product of a Cephalosporium species contained not one, but several antibiotics. One of these antibiotics, cephalosporin C.

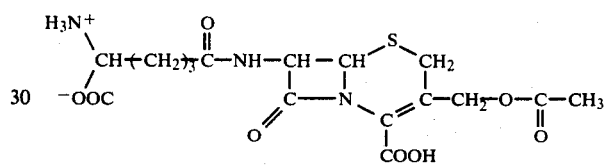

proved to be an important stepping stone in cephalosporin research. Removal of the acyl group in the 7-position of cephalosporin C yields 7-aminocephalosporanic acid,

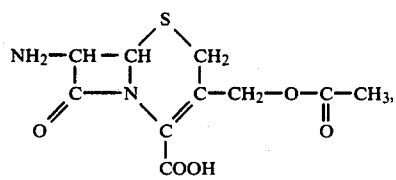

an intermediate useful for the preparation of numerous acylated compounds which are analogs of cephalosporin C.

The penicillins and cephalosporins are, of course, the most important of the β-lactam antibiotics reported to date. Others have, however, been reported. Stapley et al., Antimicrobial Agents and Chemotherapy, 2(3):122 (1972) disclose that certain actinomycete cultures isolated from soil produce antibiotics characterized by a methoxy group and a D-α-aminoadipic acid on the 7-carbon of the cephem nucleus. The cephamycins, as they are known, have the formula

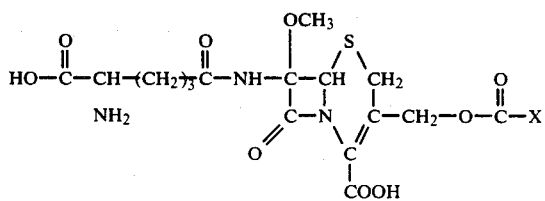

-continued

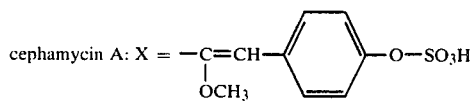
cephamycin A: X = —C=CH—⟨⟩—O—SO₃H
                    |
                    OCH₃

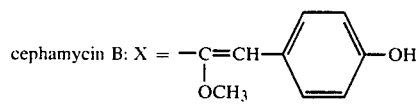
cephamycin B: X = —C=CH—⟨⟩—OH
                    |
                    OCH₃

cephamycin C: X = —NH₂.

Stapley et al. reported that cephamycin A and cephamycin B each exhibits a similar range of potencies against gram-negative and gram-positive bacteria, and cephamycin C had greater potency against gram-negative bacteria than against gram-positive bacteria. Cephamycin C was reported to be the most active of the three antibiotics.

Scannell et al., *The Journal of Antibiotics*, XXVIII(1):1 (1975), disclose the isolation from a fermentation broth of Streptomvces species 372A of (S)-alanyl-3-[α-(S)-chloro-3-(S)-hydroxy-2-oxo-3-azetidinyl-methyl]-(S)-alanine, which has the formula

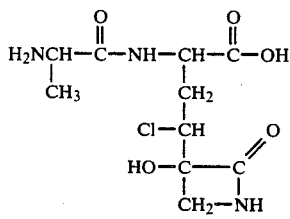

The structure of the above naturally occurring monocyclic β-lactam containing molecule is similar to the structure of the earlier discovered β-lactam containing molecules known as tabotoxins, i.e.,

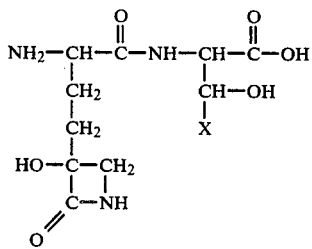

wherein X is hydrogen or methyl as reported by Stewart, *Nature*, 229:174 (1971), and Taylor et al., *Biochem. Biophys. Acta.*, 286;107 (1972).

Recently, several novel series of naturally occurring β-lactam antibiotics have been isolated. The nocardicins, nocardicin A and B, are monocyclic β-lactams having the formula

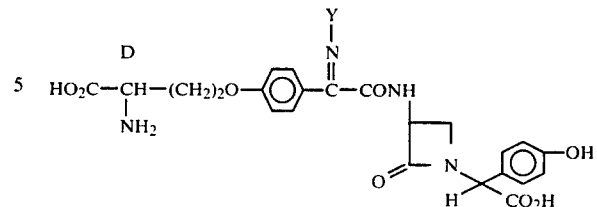

nocardicin A: Y=- syn(Z)OH
nocardicin B: Y=-anti(E)OH , as reported by Hashimoto et al., *The Journal of Antibiotics*, XXIX (9):890 (1976).

Clavulanic acid, a bicyclic β-lactam antibiotic isolated from fermentation broths of *Streptomvces clavuligerus*, has the formula

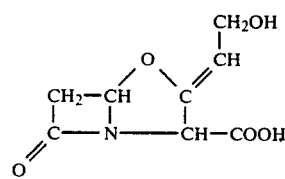

i.e., Z-(2R,5R)-3-(β-hydroxyethylidene)-7-oxo-4-oxa-1-azabicyclo[3,2,0]heptane-2-carboxylic acid, as reported by Lloyd et. al., *J.C.S. Chem. Comm.*, 266 (1976).

Still another recently isolated β-lactam antibiotic is thienamycin, an antibiotic isolated from the fermentation broths of *Streptomyces cattleya*. As reported by Albers-Schonberg et al., *J.A.C.S.*, 100:20, 6491 (1978), thienamycin has the structure

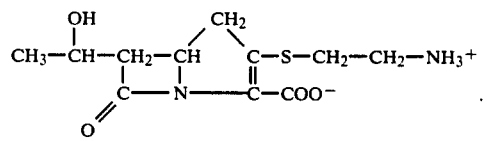

Additional fused β-lactams, olivanic acid derivatives, have recently been isolated from cultures of *Streptomyces olivaceus*. As disclosed by Brown et al., *J.C.S. Chem. Comm.*, these olivanic acid derivatives have the formulas

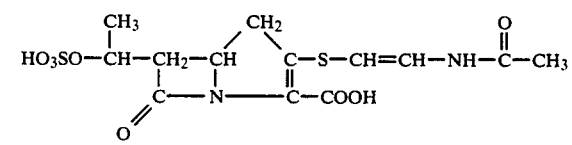

and

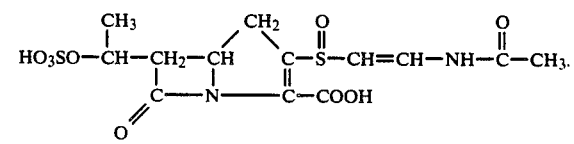

The isolation of the above antibiotics, and a discussion of their activity, is reported by Butterworth et al., *The Journal of Antibiotics*, XXXII(4):294 (1979) and by Hood et al., *The Journal of Antibiotics*, XXXII(4):295 (1979).

Another recently isolated β-lactam antibiotic is PS-5, reported by Okamura et al, *The Journal of Antibiotics*, XXXI: 480 (1978) and *The Journal of Antibiotics*, XXXII(4):262 (1979). The structure of this antibiotic, which is produced by *Streptomyces cremeus* subspecies *auratilis*, is reported to be

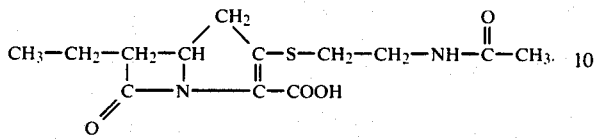

Structurally related antibiotics PS-6 and PS-7 are reported in European Patent application Ser. No. 1,567 to have the respective structures

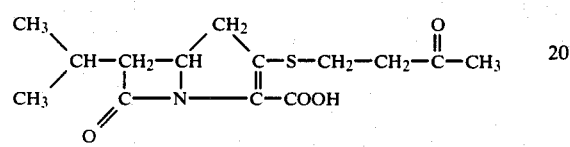

and

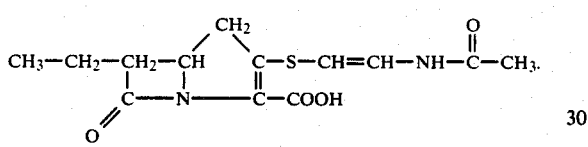

Two recently disclosed series of β-lactam antibiotics are the monocyclic β-lactams having the formulas

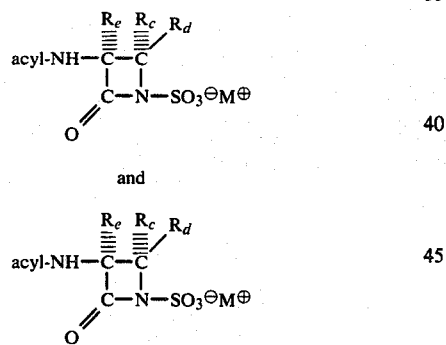

wherein $R_e$ is hydrogen or alkoxy, $R_c$ and $R_d$ are various organic substituents and $M^\oplus$ is a cation. The antibiotics having an $-SO_3^\ominus M^\oplus$ activating group are disclosed in United Kingdom patent application No. 2,071,650, published Sept. 23, 1981. The antibiotics having an $-O-SO_3^\ominus M^\oplus$ activating group are disclosed in U.S. Pat. No. 4,337,197, issued June 29, 1982.

BRIEF DESCRIPTION OF THE INVENTION

Antibacterial activity is exhibited by β-lactams having the formula

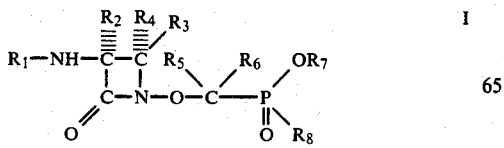

I and pharmaceutically acceptable salts thereof. As used in formula I, and throughout the specification, the symbols are as defined below.

$R_1$ is acyl;

$R_2$ is hydrogen or methoxy;

$R_3$ and $R_4$ are the same or different and each hydrogen, alkyl, alkenyl, alkynyl, cycloalkyl, phenyl, substituted phenyl or a 4,5,6 or 7-membered heterocycle (referred to hereinafter as $R_9$) or one of $R_3$ and $R_4$ is hydrogen and the other is azido, halomethyl, dihalomethyl, trihalomethyl, alkoxycarbonyl, alkenyl, alkynyl, 2-phenylethenyl, 2-phenylethynyl, carboxyl, $-CH_2X_1$ [wherein $X_1$ is azido, amino ($-NH_2$), hydroxy, alkanoylamino, phenylcarbonylamino, (substituted phenyl)carbonylamino, alkylsulfonyloxy, phenylsulfonyloxy, (substituted phenyl) sulfonyloxy, phenyl, substituted phenyl, cyano,

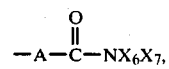

$-S-X_2$, or $-O-X_2$ (wherein A, $X_2$, $X_6$ and $X_7$ are as hereinafter defined)]. $-S-X_2$ or $-O-X_2$ [wherein $X_2$ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroarylcarbonyl].

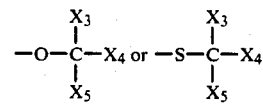

[wherein one of $X_3$ and $X_4$ is hydrogen and the other is hydrogen or alkyl, or $X_3$ and $X_4$ when taken together with the carbon atom to which they are attached form a cycloalkyl group; and $X_5$ is formyl, alkanoyl, phenylcarbonyl, (substituted phenyl)carbonyl, phenylalkylcarbonyl, (substituted phenyl) alkylcarbonyl, carboxyl, alkoxycarbonyl, aminocarbonyl

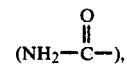

(substituted amino) carbonyl, or cyano ($-C\equiv N$)], or

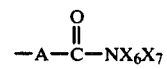

(wherein A is $-CH=CH-$, $-(CH_2)_n-$, $-CH_2-O-$, $-CH_2-NH-$, or $-CH_2-S-CH_2-$, n is 0, 1 or 2, and $X_6$ and $X_7$ are the same or different and each is hydrogen, alkyl, phenyl or substituted phenyl, or $X_6$ is hydrogen and $X_7$ is amino, substituted amino, acylamino or alkoxy, or $X_6$ and $X_7$ when taken together with the nitrogen atom to which they are attached form a 4, 5, 6 or 7-membered heterocycle);

$R_5$ and $R_6$ are the same or different and each is hydrogen, alkyl, alkenyl, alkynyl, phenyl, substituted phenyl, cycloalkyl or $R_9$, or $R_5$ and $R_6$ together with the carbon atom to which they are attached are cycloalkyl or $R_9$, or one of $R_5$ and $R_6$ is hydrogen and the other is azido, halomethyl, dihalomethyl, trihalomethyl, alkoxycarbonyl, alkenyl, alkynyl, 2-phenylethenyl, 2-phenylethynyl, carboxyl, $-CH_2X_1$, $-S-X_2$, $-O-X_2$, or

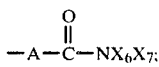

$R_7$ is hydrogen, alkyl, substituted alkyl, phenyl, substituted phenyl, 1-(ethoxycarbonyloxy) ethyl, 1,3-dihydro-3-oxo-1-isobenzofuranyl,

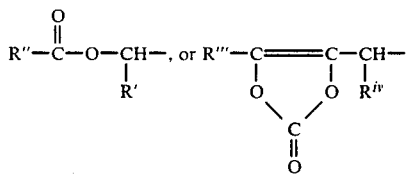

wherein R' is hydrogen or alkyl, R'' is alkyl or phenyl, R''' is hydrogen, methyl or phenyl and $R^{iv}$ is hydrogen or together with R''' is $-(CH_2)_3-$ or $-(CH_2)_5-$; and $R_8$ is hydroxy, alkoxy, (substituted alkyl)oxy, phenyloxy, (substituted phenyl)oxy, alkyl, substituted alkyl, phenyl, substituted phenyl, heteroaryl, amino, substituted amino, alkylthio, (substituted alkyl)thio, phenylthio, (substituted phenyl)thio, or

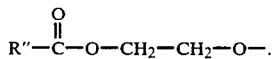

Listed below are definitions of various terms used to describe the β-lactams of this invention. These definitions apply to the terms as they are used throughout the specification (unless they are otherwise limited in specific instances) either individually or as part of a larger group, The terms "alkyl" and "alkoxy" refer to both straight and branched chain groups. Those groups having 1 to 10 carbon atoms are preferred.

The terms "cycloalkyl" and "cycloalkenyl" refer to cycloalkyl and cycloalkenyl groups having 3,4,5,6 or 7 carbon atoms.

The term "substituted alkyl" refers to alkyl groups substituted with one, or more, azido, amino ($-NH_2$), halogen, hydroxy, carboxy, cyano, alkoxycarbonyl, aminocarbonyl, alkanoyloxy, alkoxy, phenyloxy, (substituted phenyl)oxy, $R_9$-oxy, mercapto, alkylthio, phenylthio, (substituted phenyl)thio, alkylsulfinyl, or alkylsulfonyl groups.

The terms "alkanoyl", "alkenyl", and "alkynyl" refer to both straight and branched chain groups. Those groups having 2 to 10 carbon atoms are preferred.

The terms "halogen" and "halo" refer to fluorine, chlorine, bromine and iodine.

The term "substituted phenyl" refers to a phenyl group substituted with 1, 2 or 3 amino($-NH_2$), halogen, hydroxyl, trifluoromethyl, alkyl (of 1 to 4 carbon atoms), alkoxy (of 1 to 4 carbon atoms), carbamyl, or carboxyl groups.

The expression "a 4,5,6 or 7-membered heterocycle" (referred to as "$R_9$") refers to substituted and unsubstituted, aromatic and nonaromatic groups containing one or more nitrogen, oxygen or sulfur atoms. Exemplary substituents are oxo(=O), halogen, hydroxy, nitro, amino, cyano, trifluoromethyl, alkyl of 1 to 4 carbons, alkoxy of 1 to 4 carbons, alkylsulfonyl, phenyl, substituted phenyl, and substituted alkyl groups (wherein the alkyl group has 1 to 4 carbons). One type of "4,5,6 or 7-membered heterocycle" is the "heteroaryl" group. The term "heteroaryl" refers to those 4,5,6 or 7-membered heterocycles which are aromatic. Exemplary heteroaryl groups are substituted and unsubstituted pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, and tetrazolyl. Exemplary nonaromatic heterocycles (i.e., fully or partially saturated heterocyclic groups) are substituted and unsubstituted azetinyl, oxetanyl, thietanyl, piperidinyl, piperazinyl, imidazolidinyl, oxazolidinyl, pyrrolidinyl, tetrahydropyrimidinyl, dihydrothiazolyl and hexahydroazepinyl. Exemplary of the substituted 4,5,6 or 7-membered heterocycles are 1-alkyl-3-azetinyl, 2-oxo-1-imidazolidinyl, 3-alkylsulfonyl-2-oxo-1-imidazolidinyl, 3-benzylimino-2-oxo-1-imidazolidinyl, 3-alkyl-2-oxo-1-imidazolidinyl, 3-phenyl (or substituted phenyl)-2-oxo-1-imidazolidinyl, 3-benzyl-2-oxo-1-imidazolidinyl, 3-(2-aminoethyl)-2-oxo-1-imidazolidinyl, 3-amino-2-oxo-1-imidazolidinyl, 3-[(alkoxycarbonyl)amino]-2-oxo-1-imidazolidinyl, 3-[2[(alkoxycarbonyl)amino]ethyl]-2-oxo-1-imidazolidinyl, 2-oxo-1-pyrrolidinyl, 2-oxo-3-oxazolidinyl, 4-hydroxy-6-methyl-2-pyrimidinyl, 2-oxo-1-hexahydroazepinyl, 2-oxo-3-pyrrolidinyl, 2-oxo-3-furanyl, 2,3-dioxo-1-piperazinyl, 2,5-dioxo-1-piperazinyl, 4-alkyl-2,3-dioxo-1-piperazinyl, and 4-phenyl-2,3-dioxo-1-piperazinyl, The term "substituted amino" refers to a group having the formula $-NY_1Y_2$ wherein $Y_1$ is hydrogen, alkyl, phenyl, substituted phenyl, phenylalkyl or (substituted phenyl)alkyl, and $Y_2$ is alkyl, phenyl, substituted phenyl, phenylalkyl, (substituted phenyl)alkyl, hydroxy, cyano, alkoxy, phenylalkoxy, or amino ($-NH_2$).

The term "acyl" refers to all organic radicals derived from an organic acid (i.e., a carboxylic acid) by removal of the hydroxyl group. Certain acyl groups are, of course, preferred but this preference should not be viewed as a limitation of the scope of this invention. Exemplary acyl groups are those acyl groups which have been used in the past to acylate β-lactam antibiotics including 6-aminopenicillanic acid and derivatives and 7-aminocephalosporanic acid and derivatives; see, for example, *Cephalosporins and Penicillins,* edited by Flynn, Academic Press (1972), German Offenlegungsschrift No. 2,716,677, published Oct. 10, 1978, Belgian patent No. 867,994, published Dec. 11, 1978, U.S. Pat. No. 4,152,432, issued May 1, 1979, U.S. Pat. No. 3,971,778, issued July 27, 1976, U.S. Pat. No. 4,172,199, issued Oct. 23, 1979, and British patent No. 1,348,894, published Mar. 27, 1974. The portions of these references describing various acyl groups are incorporated herein by reference. The following list of acyl groups is presented to further exemplify the term "acyl"; it should not be regarded as limiting that term. Exemplary acyl groups are:

(a) Aliphatic groups having the formula

wherein $R_a$ is alkyl; cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Carbocyclic aromatic groups having the formula

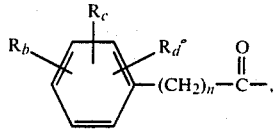

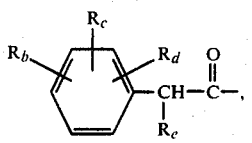

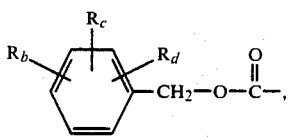

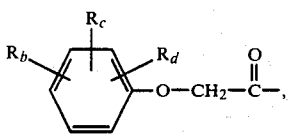

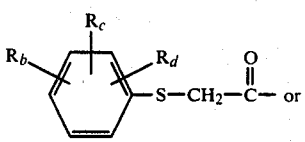

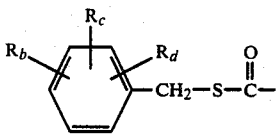

wherein n is 0, 1, 2 or 3; $R_b$, $R_c$, and $R_d$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R_e$ is amino, hydroxyl, a carboxyl salt, protected carboxyl, formyloxy, a sulfo salt, a sulfoamino salt, azido, halogen, hydrazino, alkylhydrazino, phenylhydrazino, or [(alkylthio)thioxomethyl]thio.

Preferred carbocyclic aromatic acyl groups include those having the formula

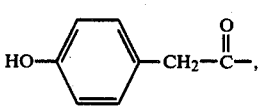

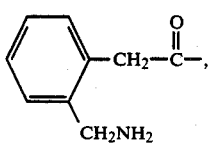

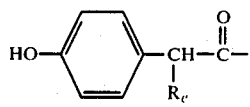

($R_e$ is preferably a carboxyl salt or sulfo salt) and

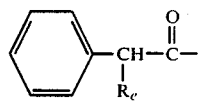

($R_e$ is preferably a carboxyl salt or sulfo salt).

(c) Heteroaromatic groups having the formula

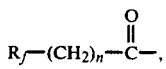

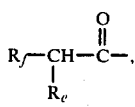

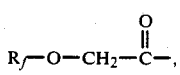

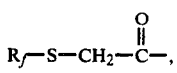

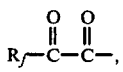

wherein n is 0, 1, 2 or 3; $R_e$ is as defined above; and $R_f$ is a substituted or unsubstituted 5-, 6- or 7-membered heterocyclic ring containing 1,2,3 or 4 (preferably 1 or 2) nitrogen, oxygen and sulfur atoms. Exemplary heterocyclic rings are thienyl, furyl, pyrrolyl, pyridinyl, pyrazolyl, pyrazinyl, thiazolyl, pyrimidinyl, thiadiazolyl and tetrazolyl. Exemplary substituents are halogen, hydroxyl, nitro, amino, protected amino, cyano, trifluoromethyl, alkyl of 1 to 4 carbon atoms, alkoxy of 1 to 4 carbon atoms, or

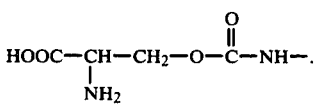

Preferred heteroaromatic acyl groups include those groups of the above formulas wherein $R_f$ is 2-amino-4-thiazolyl, 2-amino-5-halo-4-thiazolyl, 4-aminopyrimidin-2-yl, 5-amino-1,2,4-thiadiazol-3-yl, 2-thienyl, 2-furanyl, or 6-aminopyridin-2-yl.

(d) [[(4-Substituted-2,3-dioxo-1-piperazinyl)carbonyl]amino]arylacetyl groups having the formula

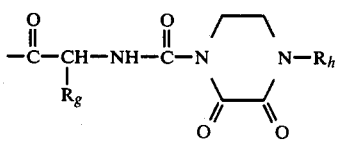

wherein $R_g$ is an aromatic group (including carbocyclic aromatics such as those of the formula

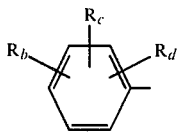

and heteroaromatics as included within the definition of $R_f$); and $R_h$ is alkyl, substituted alkyl (wherein the alkyl group is substituted with one or more halogen, cyano, nitro, amino or mercapto groups), arylmethyleneamino (i.e., —N=CH—$R_g$ wherein $R_g$ is as defined above), arylcarbonylamino (i.e.,

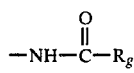

wherein $R_g$ is as defined above) or alkylcarbonylamino.

Preferred [[(4-substituted-2,3-dioxo-1-piperazinyl)carbonyl]amino]arylacetyl groups include those wherein $R_h$ is ethyl, phenylmethyleneamino or 2-furylmethyleneamino.

(e) (Substituted oxyimino)arylacetyl groups having the formula

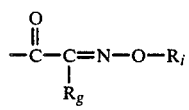

wherein $R_g$ is as defined above and $R_i$ is hydrogen, alkyl, cycloalkyl, alkylaminocarbonyl, arylaminocarbonyl (i.e.,

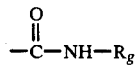

wherein $R_g$ is as defined above) or substituted alkyl (wherein the alkyl group is substituted with one or more halogen, cyano, nitro, amino, mercapto, alkylthio, aromatic group (as defined by $R_g$), carboxyl (including salts thereof), amido, alkoxycarbonyl, phenylmethoxycarbonyl, diphenylmethoxycarbonyl, hydroxyalkoxyphosphinyl, dihydroxyphosphinyl, hydroxy(phenylmethoxy)phosphinyl, or dialkoxyphosphinyl substituents).

Preferred (substituted oxyimino)arylacetyl groups include those wherein $R_g$ is 2-amino-4-thiazolyl. Also preferred are those groups wherein $R_i$ is methyl, ethyl, carboxymethyl, 1-carboxy-1-methylethyl, 2,2,2-trifluoroethyl or 1-carboxycyclopropyl.

(f) (Acylamino)arylacetyl groups having the formula

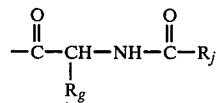

wherein $R_g$ is as defined above and $R_j$ is amino, alkylamino, (cyanoalkyl)amino, amido, alkylamido, (cyanoalkyl)amido

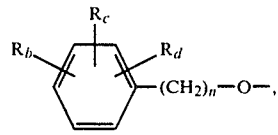

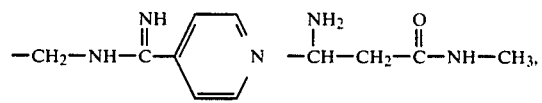

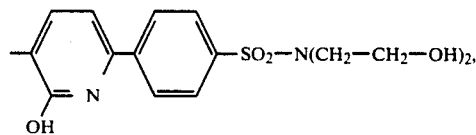

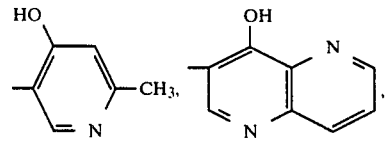

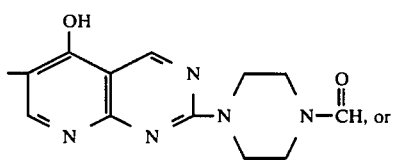

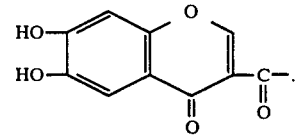

Preferred (acylamino)arylacetyl groups of the above formula include those groups wherein $R_j$ is amino or amido. Also preferred are those groups wherein $R_g$ is phenyl or 2-thienyl.

(g) [[[3-Substituted-2-oxo-1-imidazolidinyl]carbonyl]amino]arylacetyl groups having the formula

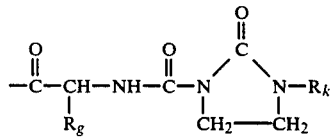

wherein $R_g$ is as defined above and $R_k$ is hydrogen, alkylsulfonyl, arylmethyleneamino (i e., —N=CH—$R_g$ wherein $R_g$ is as defined above),

wherein $R_m$ is hydrogen, alkyl or halogen substituted alkyl), aromatic group (as defined by $R_g$ above), alkyl or substituted alkyl (wherein the alkyl group is substituted with one or more halogen, cyano, nitro, amino or mercapto groups).

Preferred [[[3-substituted-2-oxo-1-imidazolidinyl]carbonyl]amino]arylacetyl groups of the above formula include those wherein $R_g$ is phenyl or 2-thienyl. Also preferred are those groups wherein $R_k$ is hydrogen, methylsulfonyl, phenylmethyleneamino or 2-furylmethyleneamino.

The compounds of this invention form basic salts with various inorganic and organic bases which are also within the scope of this invention. Such salts include ammonium salts, alkali metal salts, alkaline earth metal salts, salts with organic bases, e.g., dicyclohexylamine, benzathine, N-methyl-D-glucamine, hydrabamine and the like. The pharmaceutically acceptable salts are preferred, although other salts are also useful, e.g., in isolating or purifying the product.

Some of the compounds of this invention may be crystallized or recrystallized from solvents containing water. In these cases water of hydration may be formed. This invention contemplates stoichiometric hydrates as well as compounds containing variable amounts of water that may be produced by processes such as lyophilization.

β-Lactams having an

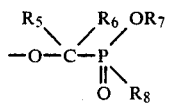

substituent in the 1-position and an amino or acylamino substituent in the 3-position contain at least one chiral center—the carbon atom (in the 3-position of the β-lactam nucleus) to which the amino or acylamino substituent is attached. This invention is directed to those β-lactams which have been described above, wherein the stereochemistry at the chiral center in the 3-position of the β-lactam nucleus is the same as the configuration at the carbon atom in the 6-position of naturally occurring penicillins (e.g., penicillin G) and as the configuration at the carbon atom in the 7-position of naturally occurring cephamycins (e.g., cephamycin C).

Also included within the scope of this invention are racemic mixtures which contain the above-described β-lactams.

DETAILED DESCRIPTION OF THE INVENTION

β-Lactams having an

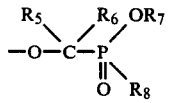

substituent in the 1-position of the β-lactam nucleus and an acylamino substituent in the 3-position of the β-lactam nucleus have activity against a range of gram-negative and gram-positive organisms.

The compounds of this invention can be used as agents to combat bacterial infections (including urinary tract infections and respiratory infections) in mammaliam species, such as domesticated animals (e.g., dogs, cats, cows, horses, and the like) and humans.

For combating bacterial infections in mammals, a compound of this invention can be administered to a mammal in need thereof in an amount of about 1.4 mg/kg/day to about 350 mg/kg/day. Preferably about 14 mg/kg/day to about 100 mg/kg/day. All modes of administration which have been used in the past to deliver penicillins and cephalosporins to the site of the infection are also contemplated for use with the novel family of β-lactams of this invention. Such methods of administration include oral, intravenous, intramuscular, and as a suppository.

The β-lactams of this invention can be prepared from an amino acid having the formula

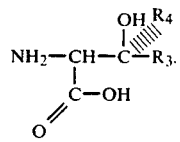

The amino group is first protected with a classical protecting group (e.g., t-butoxycarbonyl, benzyloxycarbonyl, o-nitrophenylsulfenyl, etc.), yielding a compound having the formula

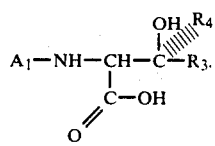

In formula III, and throughout the specification, the symbol "$A_1$" refers to a nitrogen protecting group.

The carboxyl group of a protected amino acid of formula III is then reacted with an amine salt having the formula $$Y-O-NH_3^{\oplus}Cl^{\ominus}. \qquad IV$$

In formula IV, and throughout the specification, the symbol "Y" refers to benzyl, pivaloyl, $-CH_2CH(NHA_2)CO_2alkyl$ ($A_2$ is an amino protecting group), t-butyl, p-nitrobenzyl, benzhydryl, 2-cyanoethyl, 2-trimethylsilylethyl, trichloroethyl, p-anisyl, inter alia. The reaction proceeds in the presence of a coupling agent such as 1-ethyl-3-(3-dimethylaminopropyl)carbodiimide or dicyclohexylcarbodiimide, and yields a compound having the formula

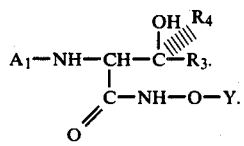

The hydroxyl group of a compound of formula V is converted to a leaving group, using, for example, a classical reagent such as methanesulfonyl chloride (methanesulfonyl is referred to hereinafter as "Ms").

The fully protected compound having the formula

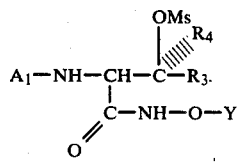

is cyclized by treatment with base, e.g., potassium carbonate. The reaction is preferably carried out in an organic solvent such as acetone, under reflux conditions, and yields a compound having the formula

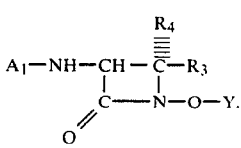　VII

Alternatively, cyclization of a compound of formula V can be accomplished without first converting the hydroxyl group to a leaving group. Treatment of a compound of formula V with triphenylphosphine and diethylazodicarboxylate or carbon tetrachloride, yields a compound of formula VII Both of the methods disclosed above for ring closure of a compound of formula V result in the inversion of the stereochemistry of the $R_3$ and $R_4$ substituents.

Selective reduction of a compound of formula VII (using catalytic hydrogenation if Y is benzyl or by treatment with a base such as sodium sulfide or sodium hydroxide if Y is pivaloyl, or with DBU if Y is $-CH_2CH(NHA_2)CO_2$alkyl yields the corresponding compound having the formula

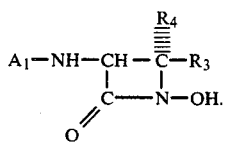　VIII

Compounds of formula VIII are described in copending U.S. patent application Ser. No. 404,945, filed Aug. 4, 1982 and some are also described in *J.A.C.S.*, 102:7026 (1980).

Alkylation of a hydroxamic acid of formula VIII with an activated form of a compound having the formula

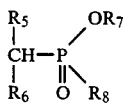　IX can be accomplished by first generating the anion of the hydroxamic acid with a suitable base, and then reacting the resulting compound with an activated form of a compound of formula IX. Activated and protected forms of compounds of formula IX have the formula

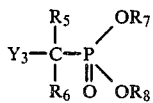　IXa wherein $Y_3$ is a suitable leaving group such as a triflate group, or other reactive leaving group well known in the art. The above alkylation procedure has been described as a two step sequence, but both steps can be performed simultaneously. The resulting product has the formula

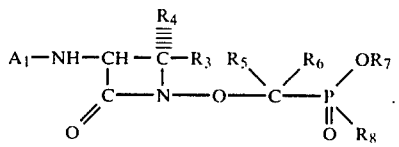　X

Deprotection of the 3-amino substituent of a compound of formula X can be accomplished using art-recognized techniques. If, for example, the protecting group is t-butoxycarbonyl, trifluoroacetic acid can be used to deprotect the amino group. If the protecting group is benzyloxycarbonyl, catalytic (e.g., palladium on charcoal) hydrogenation can be used. If the protecting group is o-nitrophenylsulfenyl, p-toluenesulfonic acid can be used in combination with p-thiocresol. The deprotected compound has the formula

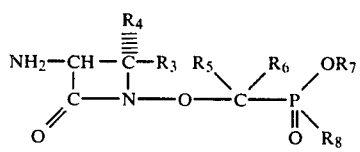　XI and is a key intermediate for preparing the compounds of this invention. The compounds of formula XI form an integral part of this invention.

Well known acylation techniques can be used to convert a compound of formula XI to the corresponding compound having the formula

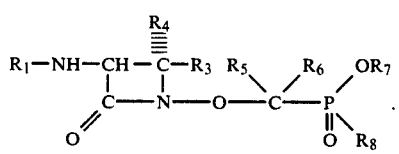　XII

Exemplary techniques include reaction with a carboxylic acid ($R_1$—OH) or corresponding carboxylic acid halide or carboxylic acid anhydride. The reactions with a carboxylic acid proceed most readily in the presence of a carbodiimide such as dicyclohexylcarbodiimide and a substance capable of forming a reactive intermediate in situ such as N-hydroxybenzotriazole or 4-dimethylaminopyridine. In those instances wherein the acyl group ($R_1$) contains reactive functionality (such as amino or carboxy groups) it may be necessary to first protect these functional groups, then carry out the acylation reaction, and finally deprotect the resulting product.

Alternatively, the compounds of this invention can be prepared by reacting a compound of formula III with an amine having the formula

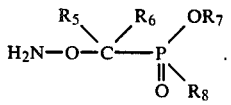　XIII

The reaction proceeds in the presence of a coupling agent such as dicyclohexylcarbodiimide and yields a compound having the formula.

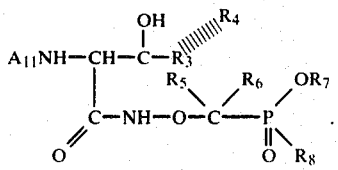

XIV

The amine of formula XIII can be prepared by reacting N-hydroxyphthalimide with an alcohol having the formula

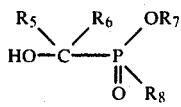

XV under Mitsunobu conditions (triphenylphosphine-diethyldiazodicarboxylate) or with an activated form of the alcohol having the formula

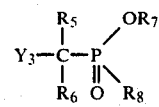

XVa to yield a compound having the formula

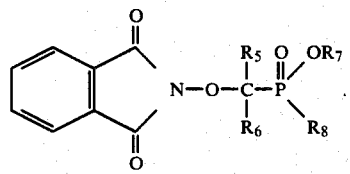

XVI

Cleavage of the phthalimide group in a compound of formula XVI with hydrazine or an alkylhydrazine yields the corresponding amine of formula XIII.

A compound of formula XIV can be cyclized to give a compound of formula X using the procedures described above for the cyclization of a compound of formula VI.

Those compounds of formula XII wherein $R_7$ is alkyl and $R_8$ is alkoxy can be coverted to the corresponding diacid having the formula

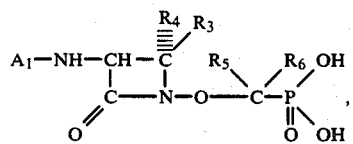

XVII providing another route for the preparation of the products of formula I wherein $R_7$ is hydrogen and $R_8$ is hydroxyl. Conversion to the diacid can be accomplished using trimethylsilyl bromide in the presence of bis-trimethylsilylacetamide as a drying agent and acid scavenger, and then solvolyzing the resulting bis-silyl ester with water or an alcohol.

Those compounds of formula XII wherein $R_7$ is alkyl and $R_8$ is alkoxy can be heated with thiourea to yield the corresponding monoacid having the formula

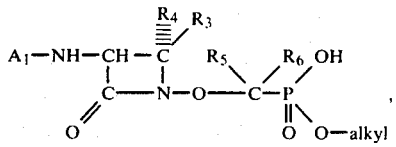

XVIII providing another route for the preparation of the products of formula I wherein $R_7$ is hydrogen and $R_8$ is alkoxy.

Alternatively, mono-acidic phosphorous derivatives can be obtained from the corresponding monoalkyl esters of formula XII, wherein $R_8$ is alkyl, substituted alkyl, phenyl, substituted phenyl, heteroaryl, amino, or substituted amino, (this subgrouping is referred to hereinafter as $R_{10}$), by treatment with an acid-scavenger and drying agent such as bis-trimethylsilylacetamide followed by treatment with trimethylsilyl bromide to yield an intermediate silyl ester having the formula

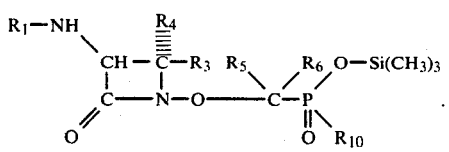

XIX

An intermediate of formula XIX can be treated with an organic or inorganic base in the presence of water or an alcohol to yield a salt of a compound having the formula

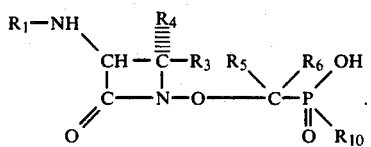

XX

The tetraalkylammonium salt of a compound of formula XX can be treated with an alkyl halide, (substituted alkyl)halide, 1-(ethoxycarbonyloxy)ethyl halide, 1,3-dihydro-3-oxo-1-isobenzofulanyl halide,

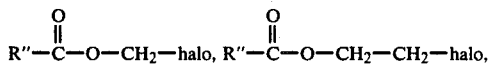

or

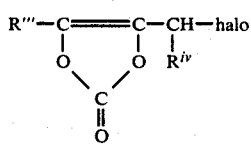

to obtain an ester having the formula

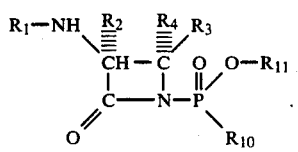

XXI wherein $R_{11}$ is alkyl, substituted alkyl, 1-(ethoxycarbonyloxy)ethyl, 1,3-dihydro-3-oxo-1-isobenzofuranyl,

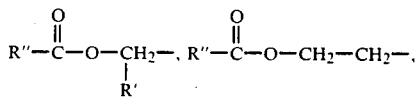

or

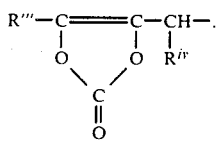

When $R_{10}$ is methoxy or ethoxy i.e., a compound of formula XVIII, this process results in transesterification, yielding the tetraalkylammonium salt of a compound having the formula

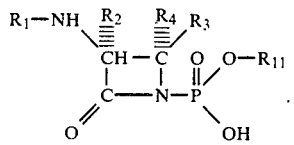

A compound of formula XXII can be converted to the corresponding compound of formula XXI wherein $R_{10}$ is methoxy or ethoxy by treating the tetraalkylammonium salt of the compound of formula XXII with methyl or ethyl sulfate. Alternatively, the tetraalkylammonium salt of the compound of formula XXII can be converted to the corresponding acid on ion-exchange resin and then treated with diazomethane or diazoethane to yield the desired compond of formula XXII wherein $R_{10}$ is methoxy or ethoxy.

The products of formula I wherein $R_2$ is methoxy can be prepared from the corresponding compound of formula VII. Halogenating (preferably chlorinating) the amide nitrogen of a compound of formula VII yields a compound having the formula

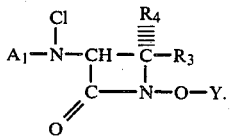

Reagents and procedures of N-chlorinating amides are known in the art. Exemplary reagents are tert.-butyl hypochlorite, sodium hypochlorite, and chlorine. The reaction can be run in an organic solvent (e.g., a lower alkanoyl such as methanol) or in a two phase solvent system (e.g., water/methylene chloride) in the presence of a base such as sodium borate decahydrate. The reaction is preferably run at a reduced temperature.

Reaction of a compound of formula XXIII with a methoxylating agent, e.g., an alkali metal methoxide, yields a compound (in combination with its enantiomer if $R_3$ and $R_4$ are the same or if XXIII is a racemic mixture) having the formula

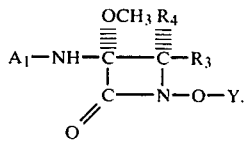

The reaction can be run in an organic solvent, e.g., a polar organic solvent such as tetrahydrofuran, at a reduced temperature.

Alternatively, a compound of formula VII can be converted to a compound of formula XXIV using a single step procedure. The methoxylating agent can first be mixed with a compound of formula VII and the N-chlorinating reagent then added to the reaction mixture.

Conversion of a compound of formula XXIV to the desired products of formula I can be accomplished using the procedures described above for the conversion of an intermediate of formula VII to a product of this invention.

The following examples are specific embodiments of this invention.

EXAMPLE 1

[3S-[3α(Z), 4β]]-[[2-Amino-4-thiazolyl)(methoxyimino)acetyl]amino
]-4-methyl-2-oxo-1-azetidinyl]oxy]methyl]phosphonic acid, potassium salt (A) N-[(Diethoxyphosphinyl)methoxy]-$N^2$-](1,1-dimethylethoxy)carbonyl]-L-threoninamide To a solution of N-t-butoxycarbonylamino-L-threonine (3.20 g, 14.6 mmol) in dimethylformamide (35 ml) was added N-hydroxybenzotriazole (1.97 g, 14.6 mmol). The resulting solution was cooled to 0° C., and dicyclohexylcarbodiimide (3.30 g, 16 mmol) was added. The ice bath was removed and the solution was stirred for thirty minutes at room temperature.

After re-cooling the solution to 0° C., diethyl aminooxymethyl phosphonate (2.67 g, 14.6 mmol) in dimethylformamide (25 ml) was added. The solution was then stirred at room temperature for 16 hours. After removal of dimethylformamide at reduced pressure, the crude product (10.6 g) was purified by two successive chromatographies on silica gel (40% acetone/methylene chloride, and 33% acetone/methylene chloride) to afford 1.76 g of the title compound.

(B) (3S trans)-[[3-[[(1,1-Dimethylethoxy)carbonyl]amino]-4-methyl-2-oxo-1-azetidinyl]oxy]methyl]-phosphonic acid, diethyl ester N-[(Diethoxyphosphinyl)methoxy]-$N^2$-[(1,1-dimethylethoxy)carbonyl]-L-threoninamide (1.38 g, 3.62 mmol) and triphenylphosphine (0.97 g, 3.7 mmol) were placed in a round-bottomed flask, which was dried in vacuo for thirty minutes at room temperature. Argon was introduced into the flask, followed by dry tetrahydrofuran (30 ml). The solution was cooled to 0° C. and diethylazodicarboxylate (585 μl, 3.7 mmol) was added dropwise. The cooling bath was removed and the solution stirred at room temperature for 16 hours.

Tetrahydrofuran was evaporated at reduced pressure, and the residue triturated with cold ether (30 ml, −10° C.) to precipitate triphenylphosphine oxide. Filtration and evaporation at reduced pressure afforded the crude product (1.96 g) which was purified by chromatography on silica gel, eluting with 20% acetone/- methylene chloride. The product obtained in this manner is conveniently separated from the 4-hydroxy-4-methyl-2-pentanone (aldol product) by crystallization from ether:pentane(1:1). The first crop of crystals thus obtained gave 0.61 g of the title compound, melting point 76°-80° C. Recrystallization from ether/pentane afforded the product, melting point 85°-88° C.

(C) [3S-[3α(Z), 4β]]-[[3-[[(2-Amino-4-thiazolyl) (methoxyimino)acetyl]amino]-4-methyl-2-oxo-1-azetidinyl]oxy]methyl]phosphonic acid, diethyl ester (3S-trans)-[[[3-[[(1,1-Dimethylethoxy)carbonyl]amino]-4-methyl-2-oxo-1-azetidinyl]oxy]methyl]phosphonic acid, diethyl ester (0.85 g, 2.32 mmol) was weighed into a round-bottomed flask under argon, and cooled to −10° C. A solution of 10% anisole in trifluoroacetic acid at −10° C. was added, and the resulting solution was stirred at that temperature for thirty minutes. Evaporation of the volatiles at room temperature with a vacuum pump afforded the crude trifluoroacetic acid salt of the deprotected azetidone starting material which was used directly in the next step.

The activated ester of (Z)-2-amino-α-(methoxyimino)-4-thiazoleacetic acid was prepared by dissolving the acid (0.47 g, 2.32 mmol) and hydroxy benzotriazole (0.31 g. 2.32 mmol) in dimethylformamide (8 ml). This solution was cooled to 0° C., and dicyclohexylcarbodiimide (0.48 g, 2.3 mmol) was added. The solution was stirred at room temperature for thirty minutes, and then cooled to 0° C. To this solution of activated ester was added the trifluoroacetic acid salt prepared above, as a solution in dimethylformamide (2.5 ml), followed by two rinses of 2.5 ml and 1.0 ml of dimethylformamide. To this solution was added triethylamine (1.0 ml, 7.2 mmol). The pH was found to be ca. 9, and the ice bath was removed.

After stirring for 16 hours at room temperature, dimethylformamide was evaporated in vacuo. The residue was treated with 5 ml of acetone, and solid potassium bicarbonate was added to adjust the pH to 6 on moist litmus paper. After filtering the solution to remove inorganic salts and hydroxybenzotriazole salt, the acetone solution was chromatographed on a reverse-phase HP-20 column (25 mm × 15") using 50% acetone/water to elute 0.47 g of the title compound, melting point 74°-78° C.

(D) [3S-[3α(Z),4β]]-[[(2-Amino-4-thiazolyl) (methoxyimino)acetyl]amino]-4-methyl-2-oxo-1-azetidinyl]oxy]methyl]phosphonic acid, potassium salt

[3S-[3α(Z), 4β]]-[[3-[[(2-Amino-4-thiazolyl) (methoxyimino)acetyl]amino]-4-methyl-2-oxo-1-azetidinyl]oxy]methyl]phosphonic acid, diethyl ester (0.10 g, 0.22 mmol) was dissolved in dry methylene chloride (2.0 ml) under argon and cooled to 0° C. To this solution was added bis(trimethylsilyl)acetamide (0.20 m, 1.12 mmol) and the solution was stirred for thirty minutes at 0° C. Trimethylsilylbromide (0.20 ml, 1.5 mmol) was added, and the cooling bath removed. Thin layer chromatography (silica. 50% acetone/methylene chloride) showed no remaining starting material after 2.5 hours, and the volatiles were evaporated in vacuo, followed by azeotropic removal of residual trimethylsilyl bromide (two times with 2 ml of toluene) at low pressure.

To the residue thus obtained was added pH 4.0 buffer (10 ml), followed by methylene chloride (10 ml). The mixture was stirred vigorously for fifteen minutes, and the aqueous layer separated, washed with methylene chloride (15 ml) and lyophilized to afford the crude product (0.11 g) which consisted predominantly of one spot by thin layer chromatography ($R_f$=0.05, 3:1:1 n-butanol:water:acetic acid). Chromatography on Hp-20 (25 mm × 12") using water as the eluting solvent afforded the title compound, melting point 220°-225° C., dec.

EXAMPLE 2

[3S-[3α(Z),4β]]-[[[3-[[(2-Amino-4-thiazolyl)(methoxyimino)acetyl]amino]-4-methyl-2-oxo-1-azetidinyl]oxy]methyl]phosphonic acid, methyl ester, potassium salt (A) (3S-trans)-[[[3-[[(1,1-Dimethylethoxy)carbonyl]amino]-4-methyl-2-oxo-1-azetidinyl]oxy]methyl]phosohonic acid, dimethyl ester (3S-trans)-[[[3-[[(1,1-Dimethylethoxy)carbonyl]amino]-4-methyl-2-oxo-1-azetidinyl]oxy]methyl]phosphonic acid, diethyl ester (250 mg, 0.68 mmol) was dissolved in dry methylene chloride (5 ml) and cooled to 0° C. under an argon atmosphere, Bistrimethylsilylacetamide (0.5 ml) was added. After stirring for 15 minutes, trimethylsilyl bromide (0.5 ml) was added to the solution, the ice bath removed, and the reaction mixture allowed to warm to room temperature over two hours. The volatiles were removed in vacuo, followed by azeotropic removal with toluene (two times with ml). The crude phosphonate bis-trimethylsilyl ester thus prepared was dissolved in dry ether (15 ml), and added to a stirring solution of diazomethane in ether/methanol (ca. 3 mmol, ether/methanol/20 ml/10 ml) at −10° C. After stirring for fifteen minutes, three drops of acetic acid were added, which failed to further discharge the pale yellow color of the reaction mixture. The solvent was then removed at reduced pressure, affording 0.40 g of the crude title compound.

The crude dimethyl phosphonate was purified by chromatography on silica gel (25 mm × 8"), eluting with 4% methanol/ethyl acetate, yielding 170 mg of the title compound of sufficient purity to be used in the next step.

(B) (3S-trans)-[[[3-[[(1,1-Dimethylethoxy)carbonyl]amino]-4-methyl-2-oxo-1-azetidinyl]oxy]methyl]phosphonic acid, methyl ester, potassium salt (3S-trans)-[[[3-[[(1,1-Dimethylethoxy)carbonyl]amino]-4-methyl-2-oxo-1-azetidinyl]oxy]methyl]phosphonic acid, dimethyl ester (170 mg, 0.50 mmol) was dissolved in deuterated acetonitrile (2.5 ml), and thiourea (45 mg, 0.59 mmol) was added. The mixture was heated in a sealed tube overnight at 80° C. Chromatography on Dowex K+ (200–400 mesh, 25 mm × 6"), using water as the eluant, followed by lyophilization of the appropriate fractions afforded the title compound (70 mg).

(C) [3S-[3α(Z),4β]]-[[[3-[[(2-Amino-4-thiazolyl)(methoxyimino)acetyl]amino]-4-methyl-2-oxo-1-azetidinyl]oxy]methyl]phosphonic acid, methyl ester, potassium salt (3S-trans)-[[[3-[[(1,1-Dimethylethoxy)carbonyl]amino]-4-methyl-2-oxo-1-azetidinyl]oxy]methyl]phosphonic acid, methyl ester, potassium salt (70 mg, 0.19 mmol) was dissolved in a solution of 10% anisole in trifluoroacetic acid (2 ml) at −10° C. The solution was stirred for thirty minutes and the volatiles removed at room temperature on a vacuum pump for three hours, to give the crude trifluoroacetic acid salt of the starting azetidinone.

Activated (Z)-2-amino-α-(methoxyimino)-4-thiazoleacetic acid was prepared by dissolving the acid (40 mg, 0.20 mmol) and hydroxybenzotriazole (27 mg, 0.20 mmol) in dimethylformamide (1 ml). After cooling the solution to −10° C. dicyclohexylcarbodiimide (45 mg, 0.22 mmol) was added and the ice bath removed. Stirring was continued for 90 minutes, after which the solution was recooled to −10° C., and the crude trifluoroacetic acid salt prepared above, was added in dimethylformamide (1 ml), followed by two rinses of dimethylformamide (1 ml, 0.5 ml). To this solution was added triethylamine (120 μl, 0.86 mmol). The solution was found to be basic by pH paper, the cooling bath was removed and the solution stirred overnight at room temperature.

Dimethylformamide was removed from the reaction mixture in vacuo, and the resulting product treated with water (1.5 ml) to afford a slurry of pH 4. Potassium bicarbonate was added to adjust the pH to 8.5, and the material was chromatographed on Dowex K+ resin (200–400 mesh, 25 mm×6″). Lyophilization of the fractions containing UV active material afforded 0.70 g of product.

This material was further purified by chromatography on HP-20 resin (25 mm×8″). Lyophilization of the appropriate fractions afforded 30 mg of the title compound. Analysis of the spectral data for this material indicated contamination of the product by hydroxybenzotriazole and dicyclohexylurea. The product browned at 164° C. and decomposed at 210° C.

EXAMPLE 3

[3S-[3α(Z),4β]]-[[[3-[[(2-Amino-4-thiazolyl) (methoxyimino)acetyl]amino]-4-methyl-2-oxo-1-azetidinyl]oxy]methyl]methylphosphinic acid, potassium salt (A) [Hydroxymethyl]methylphosphinic acid, ethyl ester Ethyl methylphosphinate (9.41 g, 0.087 mole) was heated to 85° C. under nitrogen. Dried paraformaldehyde (2.61 g, 0.078 mole) was added, and the reaction mixture was heated at 85°–95° C. for 5 minutes and then at 78° C. for 2 hours. The product was distilled at 128° C./0.9 mm to yield 7.92 g of the title compound.

(B) [[[(Trifluoromethyl)sulfonyl]oxy]methyl]methylphosphinic acid, ethyl ester

A solution of dichloromethane (2 ml), pyridine (0.23 ml, 2.65 mmole), and [hydroxymethyl]methylphosphinic acid, ethyl ester (0.37 g, 2.65 mmole) was added dropwise to triluoformethane-sulfonic anhydride (2.65 mmole, 0.45 ml) in 2 ml of dry dichloromethane at −10° C. under nitrogen. The reaction was stirred for 20 minutes at −10° C., diluted with 20 ml of dichloromethane and washed twice with 5 ml portions of water. The organic layer was dried (sodium sulfate) and concentrated in vacuo to yield 0.16 g of the title compound.

(C) [3S-(3α, 4β)]-3-[(1,1-Dimethylethoxycarbonyl)amino]-4-methyl-2-oxo-1-azetidinyl]oxy]methyl]methylphosohinic acid, ethyl ester A solution of [3S-(3α, 4β)]-3-[(2,2-dimethylethoxycarbonyl)amino]-4-methyl-2-oxo-1-hydroxyazetidine (0.155 g, 0.62 mmole) and triethylamine (0.11 ml 0.77 mmole) in dimethylformamide (1 ml) was added to [[[(trifluoromethyl)sulfonyl]oxy]methyl]methylphosphinic acid, ethyl ester (0.21 g, 0.77 mmole) at −10° C. under nitrogen. The reaction was stirred at 0° C. for 1 hour and then concentrated in vacuo. The residue was dissolved in dry dichloromethane and washed successively with pH 5.5 0.5M KH$_2$PO$_4$, pH 3.0 KH$_2$PO$_4$ buffer, and water. It was then dried (sodium sulfate) and concentrated in vacuo to yield 0.175 g of crystalline product, melting point 84°–89° C.

(D) [3S-(3α, 4β)]-3-[(1,1-Dimethylethoxycarbonyl) amino]-4-methyl-2-oxo-1-azetidinyl]oxy]methyl]methylphosphinic acid, potassium salt

[3S-(3α, 4β)]-3-[(1,1-Dimethylethoxycarbonyl)amino]-4-methyl-2-oxo-1-azetidinyl]oxy]methyl]methylphosphinic acid, ethyl ester (0.175 g, 0.52 mmole) was dissolved in 1.5 ml of dry dichloromethane and cooled to −10° C. under nitrogen. Bistrimethylsilylacetamide (BSA, 1.25 ml, 3.9 mmole) was added, and the reaction was stirred for 30 minutes at 0° C. Trimethylsilylbromide (TMSBr, 0.17 ml, 1.3 mmole) was added, and the reaction was stirred at ambient temperature for 2 hours. The reaction mixture was concentrated in vacuo, and the residue was evaporated twice from toluene. The residue was dissolved in 2 ml of tetrahydrofuran and 2 ml of 0.5M KH$_2$PO$_4$ (pH 5.5) buffer and stirred at room temperature for 1 hour at pH 5. The tetrahydrofuran was removed in vacuo and the crude aqueous solution was washed with dichloromethane. The dichloromethane solution was concentrated in vacuo to yield 77 mg of azetidinyl phosphinate starting material, and the aqueous layer was chromatographed on 60 ml of HP-20 with water and then with 10% acetone-water. The appropriate fractions were combined and lyophilized to yield 52 mg of the title compound as a solid.

(E) [3S-(3α, 4β)]-3-Amino-4-methyl-2-oxo-1-azetidinyl]oxy]methyl]methylphosphinic acid, trifluoroacetic acid salt

[3S-(3α, 4β)]-3-[(1,1-Dimethylethoxycarbonyl)amino]-4-methyl-2-oxo-1azetidinyl]oxy]methyl]methylphosphinic acid, potassium salt (50 mg, 0.15 mmole) was suspended in 0.5 ml of dichloromethane and 0.5 ml of anisole at 0° C. under nitrogen. Trifluoroacetic acid (1.0 ml) was added, and the reaction was stirred at 0° C. for 2 hours. The solution was concentrated in vacuo to a residue, which was evaporated twice from toluene to give a viscous oil. This was triturated with ether to give a white solid. The NMR spectrum of this solid in D$_2$O was consistent with that expected for the product. The D$_2$O solution was concentrated in vacuo to dryness and used in the following step.

(F) [3S-[3α(Z),4β]]-[[[3-[[(2-Amino-4-thiazolyl) methoxyimino)acetyl]amino]-4-methyl-2-oxo-1-azetidinyl]oxy]methyl]methylphosphinic acid, potassium salt (Z)-2-Amino-α-(methoxyimino)-4-thiazoleacetic acid (30.9 mg, 0.15 mmole) and 1-hydroxybenzotriazole (23.2 mg, 0.15 mmole) were dissolved in 1 ml of dimethylformamide at 0° C. under nitrogen. N,N'-Dicyclohexylcarbodiimide (DCC. 31.2 mg, 0.15 mmole) was added, and the reaction was stirred at 0° C. for 2 hours, [3S-(3α, 4β)]-3-Amino-4-methyl-2-oxo-1-azetidinyl]oxy]methyl]methylphosphinic acid, trifluoroacetic acid salt was dissolved in 3 ml of pH 5.5 0.5M KH$_2$PO$_4$ buffer, and the pH was adjusted to 5.5 with 1M potassium hydroxide. This was added to the activated ester, and the reaction was stirred at ambient temperature overnight. The reaction mixture was filtered and concentrated in vacuo. The residue was washed with dichloromethane, dissolved in water, and passed through 10 ml of Dowex 50K+ resin (0.7 m eg/ml). Fractions (4 ml) were collected, and the appropriate fractions were combined and lyophilized to a residue, which was chromatographed through 30 ml of Hp-20 using water to elute the product. After lyophilization, 21 mg of desired product was obtained, melting point 192°-202° C. dec.

What is claimed is:

1. A compound having the formula

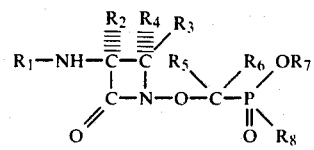

or a pharmaceutically acceptable salt thereof, wherein
$R_1$ is an acyl group derived from a carboxylic acid;
$R_2$ is hydrogen or methoxy;
$R_3$ and $R_4$ are the same or different and each is hydrogen, alkyl, alkenyl, alkynyl, cycloalkyl, phenyl, substituted phenyl or a 4,5,6, or 7-membered heterocycle or one of $R_3$ and $R_4$ is hydrogen and the other is azido, halomethyl, dihalomethyl, trihalomethyl, alkoxycarbonyl, alkenyl, alkynyl, 2-phenylethenyl, 2-phenylethynyl, carboxyl —$CH_2X_1$, —S—$X_2$,

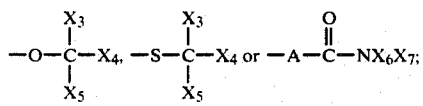

wherein $X_1$ is azido, amino, hydroxy, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

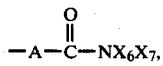

—S—$X_2$ or —O—$X_2$; $X_2$ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroarylcarbonyl; one of $X_3$ and $X_4$ is hydrogen and the other is hydrogen or alkyl, or $X_3$ and $X_4$ when taken together with the carbon atom to which they are attached form a cycloalkyl group; $X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl, (substituted amino)carbonyl, or cyano; A is —CH=CH—, —$(CH_2)_n$—, —$CH_2$—O—, —$CH_2$—NH— or —$CH_2$—S—$CH_2$—; n is 0, 1 or 2; and $X_6$ and $X_7$ are the same or different and each is hydrogen, alkyl, phenyl or substituted phenyl, or $X_6$ is hydrogen and $X_7$ is amino, substituted amino or alkoxy, or $X_6$ and $X_7$ when taken together with the nitrogen atom to which they are attached form a 4, 5, 6 or 7-membered heterocycle;

$R_5$ and $R_6$ are the same or different and each is hydrogen, alkyl, alkenyl, alkynyl, phenyl, substituted phenyl, cycloalkyl or a 4, 5, 6 or 7-membered heterocycle, or $R_5$ and $R_6$ together with the carbon atom to which they are attached are cycloalkyl or a 4, 5, 6 or 7-membered heterocycle, or one of $R_5$ and $R_6$ is hydrogen and the other is azido, halomethyl, dihalomethyl, trihalomethyl, alkoxycarbonyl, alkenyl, alkynyl, 2-phenylethenyl, 2-phenylethynyl, carboxyl, —$CH_2X_1$, —S—$X_2$, —O—$X_2$, or

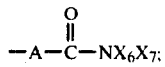

$R_7$ is hydrogen, alkyl, substituted alkyl, phenyl, substituted phenyl, 1-(ethoxycarbonyloxy)ethyl, 1,3-dihydro-3-oxo-1-isobenzofuranyl,

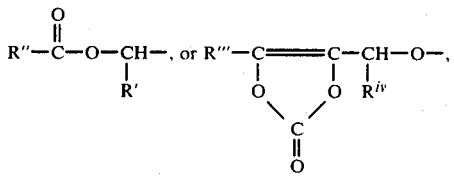

wherein $R'$ hdyrogen or alkyl, $R''$ is alkyl or phenyl, $R'''$ is hydrogen, methyl or phenyl, and $R^{iv}$ is hydrogen or together with $R'''$ is —$(CH_2)_3$— or —$(CH_2)_5$—; and $R_8$ is hydroxy, alkoxy, (substituted alkyl)oxy, phenyloxy, (substituted phenyl)oxy, alkyl, substituted alkyl, phenyl, substituted phenyl, heteroaryl, amino, substituted amino, alkylthio, (substituted alkyl)thio, phenylthio, (substituted phenyl)thio, or

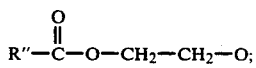

wherein the terms "alkyl" and "alkoxy" refer to groups having 1 to 10 carbon atoms;
the term "cycloalkyl" refers to groups having 3, 4, 5, 6 or 7 carbon atoms;
the terms "alkanoyl", "alkenyl", and "alkynyl" refer to groups having 2 to 10 carbon atoms;
the term "substituted phenyl" refers to a phenyl group substituted with 1, 2 or 3 amino, halogen, hydroxyl, trifluoromethyl, alkyl of 1 to 4 carbon atoms, alkoxy of 1 to 4 carbon atoms or carboxyl groups;
the term "substituted alkyl" refers to alkyl groups substituted with one or more azido, amino, halogen, hydroxy, carboxy, cyano, alkoxycarbonyl, aminocarbonyl, alkanoyloxy, alkoxy, phenyloxy, (substituted phenyl)oxy, (4, 5, 6 or 7-membered heterocycle)oxy, mercapto, alkylthio, phenylthio, (substituted phenyl)thio, alkylsulfinyl or alkylsulfonyl groups;
the term "heteroaryl" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl or one of the above groups substituted with one or more oxo, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, or substituted alkyl, wherein the alkyl group has 1 to 4 carbon atoms, groups;
the term "a 4, 5, 6 or 7-membered heterocycle" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazoyl, triazinyl, tetrazolyl, azetinyl, oxetanyl, thietanyl, piperidinyl, piperazinyl, imidazolidinyl, oxazolidinyl, pyrrolidinyl, tetrahydropyrimidinyl, dihydrothiazolyl or hexahydroazepinyl or one of the above groups substituted with one or more oxo, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, or substituted alkyl, wherein the alkyl group has 1 to 4 carbon atoms, groups; and the term "substituted amino" refers to a group having the formula $-NY_1Y_2$ wherein $Y_1$ is hydrogen, alkyl, phenyl, substituted phenyl, phenylalkyl or (substituted phenyl)alkyl, and $Y_2$ is alkyl, phenyl, substituted phenyl, phenylalkyl, (substituted phenyl)alkyl, hydroxy, cyano, alkoxy, phenylalkoxy or amino.

2. A compound in accordance with claim 1 wherein $R_2$ is hydrogen.

3. A compound in accordance with claim 1 wherein $R_3$ and $R_4$ are the same or different and each is hydrogen or alkyl.

4. A compound in accordance with claim 2 wherein $R_3$ and $R_4$ are the same or different and each is hydrogen or alkyl.

5. A compound in accordance with claim 1 wherein $R_5$ and $R_6$ are the same or different and each is hydrogen or alkyl.

6. A compound in accordance with claim 2 wherein $R_5$ and $R_6$ are the same or different and each is hydrogen or alkyl.

7. A compound in accordance with claim 1 wherein $R_7$ is hydrogen or alkyl and $R_8$ is hydroxy or alkoxy.

8. A compound in accordance with claim 2 wherein $R_7$ is hydrogen or alkyl and $R_8$ is hydroxy or alkoxy.

9. A compound in accordance with claim 1 wherein $R_2$ is hydrogen;
$R_3$ and $R_4$ are the same or different and each is hydrogen or alkyl;
$R_5$ and $R_6$ are the same or different and hydrogen or alkyl;
$R_7$ is hydrogen or alkyl; and
$R_8$ is hydroxy or alkoxy.

10. A compound in accordance with claim 1, [3S-[3α(Z),4β]]-[[[3-[[(2-amino-4-thiazolyl) (methoxyimino)acetyl]amino]-4-methyl-2-oxo-1-azetidinyl]oxy]methyl]phosphonic acid, or a salt thereof.

11. A compound in accordance with claim 1, [3S-[3α(Z),4β]]-[[[3-[[(2-Amino-4-thiazolyl) (methoxyimino)acetyl]amino]-4-methyl-2-oxo-1-azetidinyl]oxy]methyl]phosphonic acid, methyl ester, or a salt thereof.

12. A compound in accordance with claim 1, [3S-[3α(Z),4β]]-[[[3-[[(2-Amino-4-thiazolyl) (methoxyimino)acetyl]amino]-4-methyl-2-oxo-1-azetidinyl]oxy]methyl]phosphonic acid, diethyl ester or a salt thereof.

13. A compound in accordance with claim 1, [3S-[3α(Z),4β]]-[[[3-[[(2 Amino-4-thiazolyl) (methoxyimino)acetyl]amino]-4-methyl-2-oxo-1-azetidinyl]oxy]methyl]methylphosphinic acid, or a salt thereof.

14. A compound having the formula

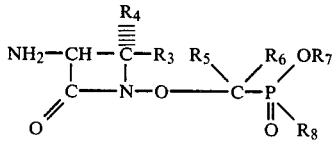

wherein
$R_3$ and $R_4$ are the same or different and each is hydrogen, alkyl, alkenyl, alkynyl, cyclocalkyl, phenyl substituted phenyl or a 4, 5, 6 or 7-membered heterocycle or one of $R_3$ and $R_4$ is hydrogen and the other is azido, halomethyl, dihalomethyl, trihalomethyl, alkoxycarbonyl, alkenyl, alkynyl, 2-phenylethenyl, 2-phenylethynyl, carboxyl, $-CH_2X_1$, $-S-X_2$, $-O-X_2$,

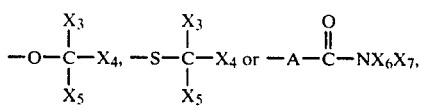

$-S-X_2$, wherein $X_1$ is azido, amino, hydroxy, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

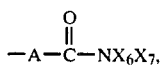

or $-O-X_2$; $X_2$ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroarylcarbonyl; one of $X_3$ and $X_4$ is hydrogen and the other is hydrogen or alkyl, or $X_3$ and $X_4$ when taken together with the carbon atom to which they are attached form a cycloalkyl group; $X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl, (substituted amino)carbonyl, or cyano; A is $-CH=CH-$, $-(CH_2)_n-$, $-CH_2-O-$, $-CH_2-NH-$ or $-CH_2-S-CH_2-$; n is 0, 1 or 2; and $X_6$ and $X_7$ are the same or different and each is hydrogen, alkyl, phenyl or substituted phenyl, or $X_6$ is hydrogen and $X_7$ is amino, substituted amino or alkoxy, or $X_6$ and $X_7$ when taken together with the nitrogen atom to which they are attached form a 4, 5, 6 or 7-membered heterocycle;

$R_5$ and $R_6$ are the same or different and each is hydrogen, alkyl, alkenyl, alkynyl, phenyl, substituted phenyl, cycloalkyl or a 4, 5, 6 or 7-membered heterocycle, or $R_5$ and $R_6$ together with the carbon atom to which they are attached are cycloalkyl or a 4, 5, 6 or 7-membered heterocycle, or one of $R_5$ and $R_6$ is hydrogen and the other is azido, halomethyl, dihalomethyl, trihalomethyl, alkoxycarbonyl, alkenyl, alkynyl, 2-phenylethenyl, 2-phenylethynyl, carboxyl, $-CH_2X_1$, $-S-X_2$, $-O-X_2$, or

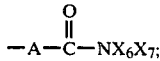

$R_7$ is hydrogen, alkyl, substituted alkyl, phenyl, substituted phenyl, 1-(ethoxycarbonyloxy)ethyl, 1,3-dihydro-3-oxo-1isobenzofuranyl,

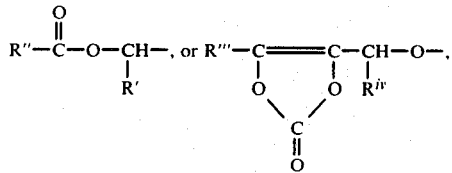

wherein R' is hydrogen or alkyl, R" is alkyl or phenyl, R'" is hydrogen, methyl or phenyl, and $R^{iv}$ is hydrogen or together with R'" is —$(CH_2)_3$— or —$(CH_2)_5$—; and $R_8$ is hydroxy, alkoxy, (substituted alkyl)oxy, phenyloxy, (substituted phenyl)oxy, alkyl, substituted alkyl, phenyl, substituted phenyl, heteroaryl, amino, substituted amino, alkylthio, (substituted alkyl)thio, phenylthio, (substituted phenyl)thio,

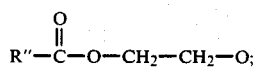

wherein the terms "alkyl" and "alkoxy" refer to groups having 1 to 10 carbon atoms;

the term "cycloalkyl" refers to groups having 3, 4 5, 6 or 7 carbon atoms;

the terms "alkanoyl", "alkenyl", and "alkynyl" refer to groups having 2 to 10 carbon atoms;

the term "substituted phenyl" refers to a phenyl group substituted with 1, 2 or 3 amino, halogen, hydroxyl, trifluoromethyl, alkyl of 1 to 4 carbon atoms, alkoxy of 1 to 4 carbon atoms or carboxy groups;

the term "substituted alkyl" refers to alkyl groups substituted with one or more azido, amino, halogen, hydroxy, carboxyl, cyano, alkoxycarbonyl, aminocarbonyl, alkanoyloxy, alkoxy, phenyloxy, (substituted phenyl)oxy, (4, 5, 6 or 7-membered heterocycle)oxy, mercapto, alkylthio, phenylthio, (substituted phenyl)thio, alkylsulfinyl or alkylsulfonyl groups;

the term "heteroaryl" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl or one of the above groups substituted with one or more halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, or substituted alkyl, wherein the alkyl group has 1 to 4 carbon atoms, groups;

the term "a 4, 5, 6 or 7-membered heterocycle" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazoyl, triazinyl, tetrazolyl, azetinyl, oxetanyl, thietanyl, piperidinyl, piperazinyl, imidazolidinyl, oxazolidinyl, pyrrolidinyl, tetrahydropyrimidinyl, dihydrothiazolyl or hexahydroazepinyl or one of the above groups substituted with one or more oxo, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, or substituted alkyl, wherein the alkyl group has 1 to 4 carbon atoms, groups; and the term "substituted amino" refers to a group having the formula —$NY_1Y_2$ wherein $Y_1$ is hydrogen, alkyl, phenyl, substituted phenyl, phenylalkyl or (substituted phenyl)alkyl, and $Y_2$ is alkyl, phenyl, substituted phenyl phenylalkyl, (substituted phenyl)alkyl, hydroxy, cyano, alkoxy, phenylalkoxy or amino.

* * * * *